United States Patent
Samuels et al.

[11] 3,976,079
[45] Aug. 24, 1976

[54] SECURING DEVICES FOR SUTURES

[76] Inventors: Peter B. Samuels, 14708 Sutton St., Sherman Oaks, Calif. 91316; Ernest C. Wood, 2461 Ivanhoe Drive, Los Angeles, Calif. 90039

[22] Filed: May 6, 1975

[21] Appl. No.: 575,004

Related U.S. Application Data

[63] Continuation-in-part of Ser. No. 493,759, Aug. 1, 1974, abandoned.

[52] U.S. Cl. ............................. 128/335; 24/115 M; 24/136 R; 403/379
[51] Int. Cl.² ........................................ A61B 17/04
[58] Field of Search ....................... 128/334 R, 335; 24/115 M, 134, 136 R; 403/13, 14, 319, 354, 378, 379; 43/44.91, 44.93

[56] References Cited
UNITED STATES PATENTS

| | | | |
|---|---|---|---|
| 166,022 | 7/1875 | Mihills | 24/136 R |
| 459,513 | 9/1891 | Montz | 24/136 R |
| 1,852,098 | 4/1932 | Anderson | 128/335 |
| 2,075,508 | 3/1937 | Davidson | 128/335 |
| 2,579,713 | 12/1951 | Tolle | 43/44.91 |
| 2,711,801 | 6/1955 | Super et al. | 403/379 X |
| 3,541,591 | 11/1970 | Hoegerman | 128/335 |
| 3,589,052 | 6/1971 | King | 24/134 R |
| 3,664,345 | 5/1972 | Dabbs et al. | 128/335 |

*Primary Examiner*—Dalton L. Truluck
*Attorney, Agent, or Firm*—McDougall, Hersh & Scott

[57] ABSTRACT

Devices for releasably securing externally located sutures are disclosed. These devices may be utilized, for example, to maintain a retention suture in place over an abdominal incision. According to a first configuration, the devices have button-like bodies and have slots therethrough for receiving the suture. Means for securing the suture to the device pass into the slot and compress the suture against the body. According to a second construction, a bridge device is utilized wherein the sutures are received in slots on the bridge where they are secured by compression members.

6 Claims, 18 Drawing Figures

SECURING DEVICES FOR SUTURES

This application is a continuation-in-part of application Ser. No. 493,759, filed Aug. 1, 1974, now abandoned.

BACKGROUND OF THE INVENTION

This invention relates to the field of surgical devices and, in particular, to those devices utilized for temporarily securing sutures. At present, in order to close major incisions into a human or an animal, heavy externally secured sutures known as retention sutures are utilized in addition to the permanent internal sutures. Such retention sutures are passed through all tissue layers and serve as a safety binding providing additional support to the wound during the initial healing period. Additionally, should the healing process not progress as rapidly as expected owing to infection, poor circulation or other reasons, the retention sutures will support the wound and prevent it from breaking open. Normally, a retention suture is passed circumferentially around the wound and emerges on either side thereof where it is tied just tightly enough so that it lays flush against the surface of the skin.

One problem associated with the use of retention sutures is the compression and scarring of the skin caused by their prolonged presence. In order to reduce this problem rubber cuffs have been used, as well as gauze wrapped around the sutures. Additional techniques for reducing scarring include the use of a supportive plastic bridge to prevent the sutures from cutting into the tissue.

Another problem which arises in using retention sutures is due to swelling of the wound whereby the circumferentially tide suture becomes tighter, causing irritation and further swelling, thereby interfering with drainage from the affected area. Still another problem is the difficulty of installing a circumferential retention suture with the right tension. The tension on the suture usually requires adjustment over a period of time but present securing methods do not allow for this. For example, these sutures have been secured by knotting them. Thus, it is difficult if not impossible to allow for future swelling or shrinkage of the tissues. Subsequently, when such swelling or shrinkage occurs, improper tension is present such that the suture is too tight or that it is not tight enough to effectively perform its function.

A final problem created by the inability to adjustably secure the suture in position arises from the fact that retention sutures are usually placed in position around the wound before the permanent internal sutures. Thus, during the period when the permanent sutures are being installed, the retention sutures must be left hanging and untensioned since they cannot be adjusted until the permanent sutures are in position. Permitting these sutures to remain hanging permits them to tangle and slip out of position.

OBJECTS OF THE INVENTION

It is accordingly an object of the present invention to provide a releasable securing device for sutures.

It is another object of the present invention to provide a releasable securing device for sutures which may be adjusted so that the tension on the suture may be maintained at a desired level.

It is a further object of the present invention to provide a suture securing device which permits the exact adjustment of tension on a suture and which may be repeatedly readjusted to account for changes in the condition of the tissues.

It is yet another object of the present invention to provide an adjustable suture securing device which may be utilized to secure a retention suture in place temporarily during the installation of permanent sutures and then may be readjusted to the proper tension after installation of the permanent sutures.

It is a further object of the present invention to provide a suture securing device that avoids compressing and scarring of the surface tissue.

Other objects and advantages of the present invention will be apparent from the concluding portion of the specification.

DETAILED DESCRIPTION

Figure 1:
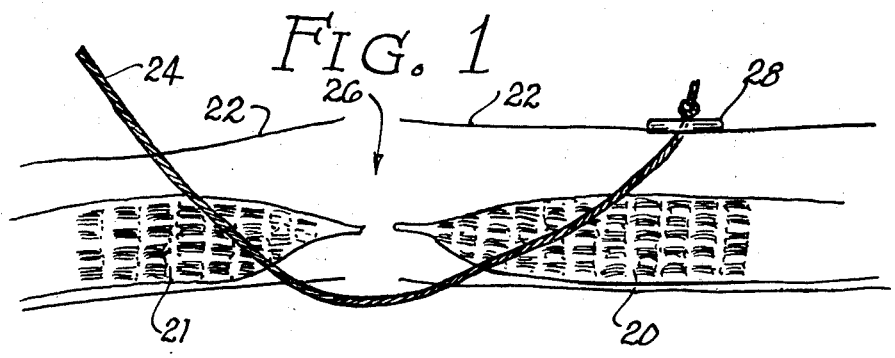
FIG. 1 is an illustration of an abdominal incision wherein a retention suture has been passed through the incision area prior to installing the permanent internal sutures.

Referring to FIG. 1, a simplified illustration of an abdominal incision is illustrated. The abdominal walls are identified by the numerals 20 and 21 while the surface tissues are indicated by the numeral 22. A retention suture 24 is illustrated as passing circumferentially through the incision area 26 including both sections 20 and 21 of the abdominal wall and up through the surface tissues 22. On one side of the incision the retention suture is secured by a button-like device 28. This device has a single aperture through its center and after the suture is passed therethrough, it is knotted so that the button permanently secures one end of the retention suture 24. The button device 28 is not part of the present invention.

Retention sutures are generally installed circumferentially around the wound prior to providing the permanent internal sutures. The one or more retention sutures which are utilized, depending on the size of the wound, act to provide support and prevent the incision from breaking open during the early stages of healing.

Figure 2:
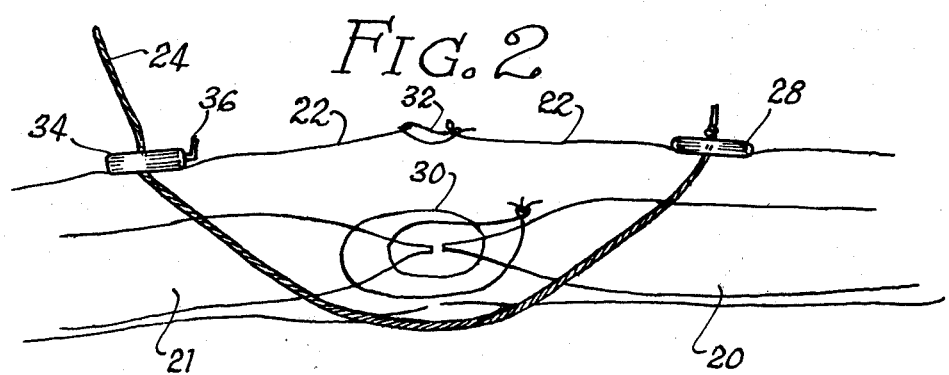
FIG. 2 illustrates the abdominal incision at a later point in time wherein the permanent sutures have been installed and tension has been applied to the retention sutures, utilizing a securing device according to the present invention.

Referring now to FIG. 2, the incision of FIG. 1 is shown at a latter stage of surgery. At this point, the permanent sutures 30 have been installed along the edge of the abdominal wall nearest the incision and the surface tissue 22 has been rejoined by stitching material 32. As further indicated in FIG. 2, the left-hand end of the retention suture 24 has now been secured by a button-like device 34 according to the present invention. As will be described, this device permits the tension on the suture 24 to be adjusted by the surgeon as desired. When a satisfactory tension has been obtained, a pin member 36 is utilized for compressing the suture against the body of the button member 34 to prevent slipping of the suture through the button member. Thus, as illustrated in FIG. 2, a closed incision will have permanent internal sutures 30, surface tissue sutures 32 and temporary retention sutures 24 which support the incision until the healing of the abdominal wall and the surface tissue have progressed to a point where there is no likelihood of the incision ripping open. When no longer needed, the retention sutures 24 are removed simply by releasing the pin member 36 and removing the button member 34 from the suture. The suture may then be removed from the wound.

Figure 3:
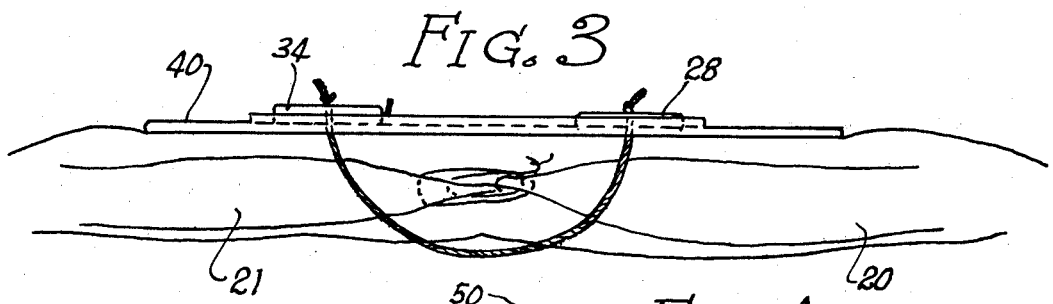
FIG. 3 is a view similar to FIG. 2 illustrating the use of a securing device according to the present invention in conjunction with a bridge device.

Referring to FIG. 3, a closed incision similar to that illustrated in FIG. 2 is shown. In this instance, however, the permanent button 28 and the releasable button 34 of the present invention are mounted on a bridge-like device 40. This relationship is illustrated most clearly in FIG. 9. The bridge 40 is preferably formed of a plastic material which has some yield or give to it and is provided with a plurality of transverse slots 42. Depending upon the location of the retention sutures, an appropriate pair of slots 42 are selected and the sutures passed therein. The permanent button 28 and the releasable button 34 are then seated on the bridge between retaining members 44 and 46 which prevent the buttons from sliding off of the bridge. The purpose of the bridge member as best illustrated in FIG. 3 is to spread the tension of the sutures over a wide body area to reduce the discomfort and pressure of the retention suture. This may be easily understood by comparison of FIG. 2 where the buttons depress the skin over a small surface area and FIG. 3 where the bridge member distributes the pressure over a larger surface area.

Figure 7:
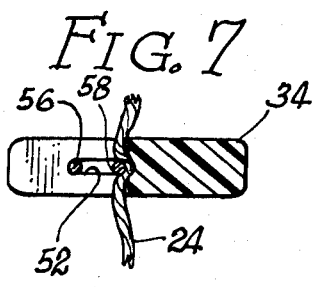
FIG. 7 is a view taken along the lines 7—7 of FIG. 6.
Figure 8:
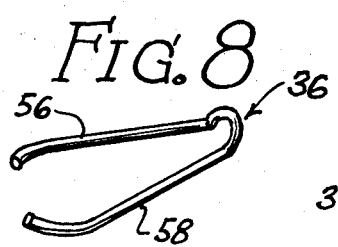
FIG. 8 is a perspective view of the spring clip utilized in the FIG. 4 device.
Figure 6:
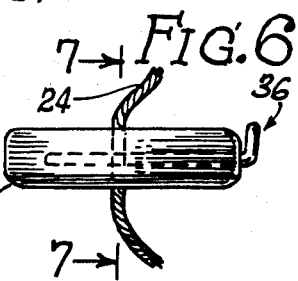
FIG. 6 is a side view of the FIG. 4 embodiment.

Referring now to FIGS. 4–8, the releasable securing device according to a preferred embodiment of the invention is illustrated. A body 34 of the device is preferably cylindrically shaped. A slot 50 is provided from the outer circumference to a point at or beyond the midpoint of the body. The slot 50 is adapted to receive a suture 24 therein as illustrated in FIGS. 6 and 7. The slot 50 flares outwardly near the end of the body to facilitate entry of the suture therein.

Figures 4, 5:
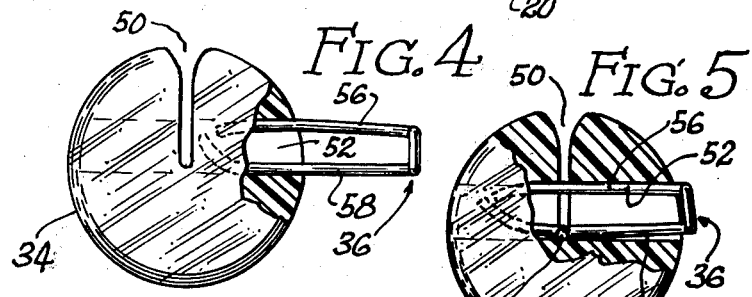
FIG. 4 is a top view of a securing device according to a first embodiment of the invention.
FIG. 5 is a bottom view of the FIG. 4 embodiment.

As best shown in FIG. 7, a hollow channel 52 extending through the device and intersecting the slot is provided. The channel is offset from the center slightly, being closer to the side of the device where the slot opening is provided. The channel is adapted to receive a metal compression clip 36 therein as indicated in FIGS. 4 and 5. In order to insert the clip the leg members 56 and 58 must be compressed towards each other until their dimension will pass into the channel 52. Once in the channel, the compression of the clip 36 creates a strong tension force against the channel walls. This force is utilized to secure the suture in the device.

Figure 9:
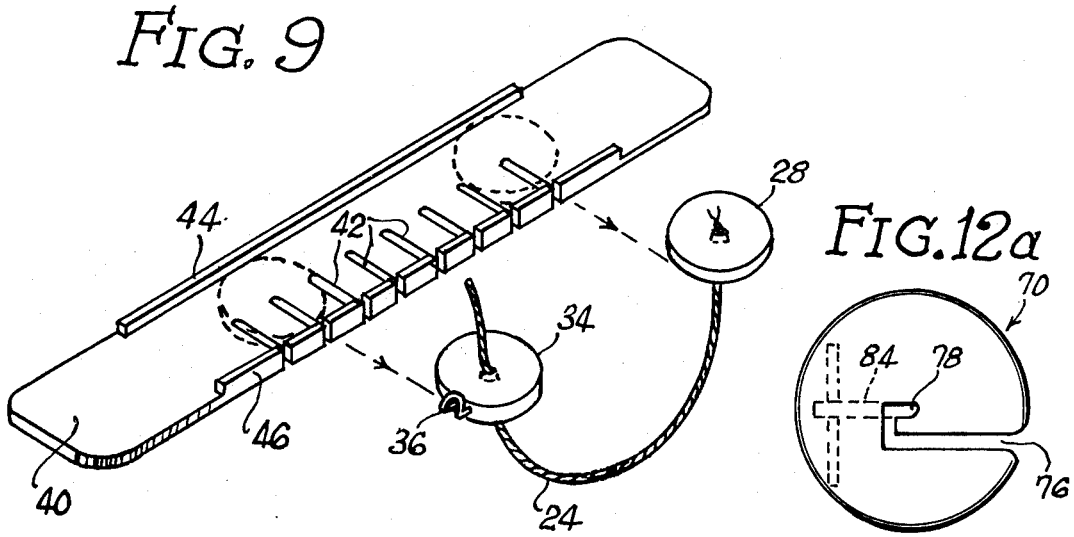
FIG. 9 is a perspective view of a retention suture having the securing device of the present invention attached thereto and illustrating the positioning of the invention on a bridge member.

In use, a suture is passed fully into the slot 50. The spring clip 36 is preferably partially inserted before the suture is placed in the slot. After the suture has been aligned in the slot, the spring clip 36 is then fully inserted into the channel 52 such that the curved leg 58 of the clip compresses the suture against the body of the securing device, as best illustrated in FIGS. 6 and 7. To remove the device from the suture, it is only necessary that the tension clip 36 be retracted either partially or fully until the leg member 58 no longer compresses the suture. Thus, the tension on the suture can be repeatedly adjusted as desired and the device can be repositioned as necessary. If desired, where it is not contemplated to use a bridge such as shown in FIG. 9, one side of the body 34 may have a soft latex layer or other material placed thereon to reduce the possibility of skin irritation when the button is sitting on surface tissue.

Figure 10:
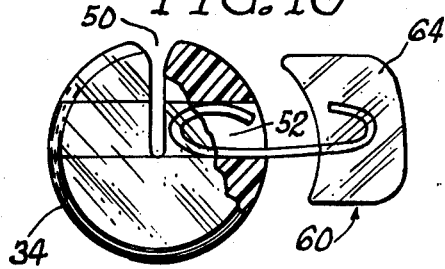
FIG. 10 is a top view of a securing device according to a second embodiment.

Referring now to FIG. 10, a releasable securing device according to a second embodiment is disclosed. In this embodiment, the body 34 may be identical with that shown in FIG. 4, having a channel 52 and a slot 50 for receiving a suture therein. In this embodiment, however, in place of the metallic compression clip 36, a tab clip 60 is utilized. Clip 60 has a first end 62 bent backwardly on itself and of a dimension just slightly larger than the channel opening 52. Connected to the other end of the clip is a tab 64 which may be desirably formed of a plastic material into which the clip is embedded. This configuration permits somewhat better control of the device than does the FIG. 4 embodiment due to the large pull tab provided. Clip 60 secures a suture against the body of the device in the same manner as the FIG. 4 embodiment.

Figure 11:
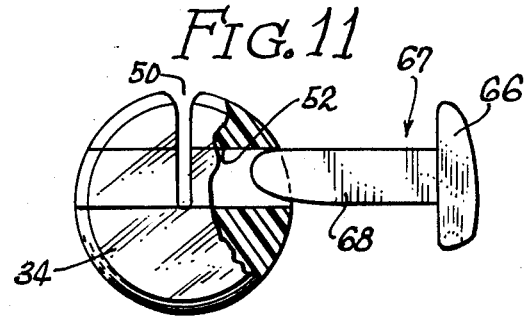
FIG. 11 is a top view of a securing device according to a third embodiment of the invention.

Referring now to FIG. 11, a third embodiment of the invention is illustrated. In this embodiment again the body 34 may be identical to the FIG. 4 construction. In this embodiment, however, a plastic tensioning member 67 is utilized in place of a compression clip. The tensioning member has a tab 66 for insertion and removal from the body 34 and a curved tongue portion 68 which serves to compress the suture against the body of the device in a manner similar to the previous embodiments.

Figure 12A:
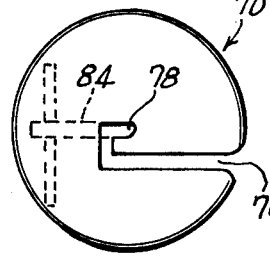
FIG. 12A is a bottom view of the FIG. 12 device illustrating the slot configuration.
Figure 12:
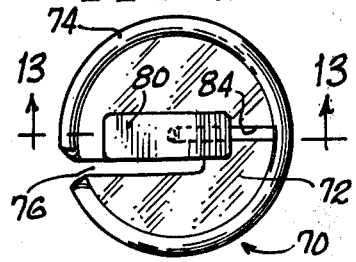
FIG. 12 is a top view of a securing device according to a fourth embodiment of the invention.
Figure 13:
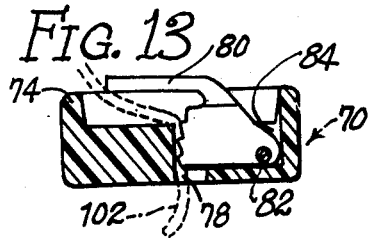
FIGS. 13 and 14 are cross-sectional views of the device of FIG. 12 indicating the manner in which the device secures a suture therein.
Figure 14:
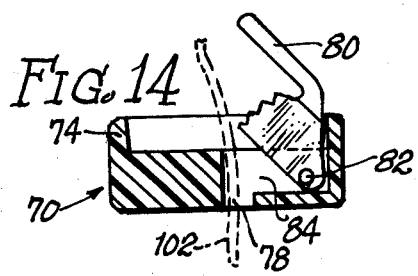

Referring now to FIGS. 12–14, a fourth embodiment of the invention is disclosed. In this embodiment, the body of the device 70 has a central portion 72 recessed beneath a circumferential rim 74. The body is provided with a slot 76 which is hook shaped, as indicated in FIG. 12A. The hook portion 73 has a ratchet tab 80 disposed above it. The ratchet tab is rotatably mounted to the body on a pin 82 journaled through the body 70 transversely of the slot. Accordingly, the ratchet tab 80 is pivotable about the pin 82 from a raised position illustrated in FIG. 14 to a lowered position (FIG. 13). In order to permit the tab 80 to engage a suture, a channel 84 partially penetrates the body 70 to accommodate the lower portion 83 of the tab 80. Thus when a suture is placed in the hooked portion 78 of the channel 76, the ratchet tab 80 having a plurality of ratchet teeth 86 thereon is pressed down onto the suture so that the teeth engage it. This compresses the suture against the body wall producing a condition where the suture will not slip.

Figure 15:
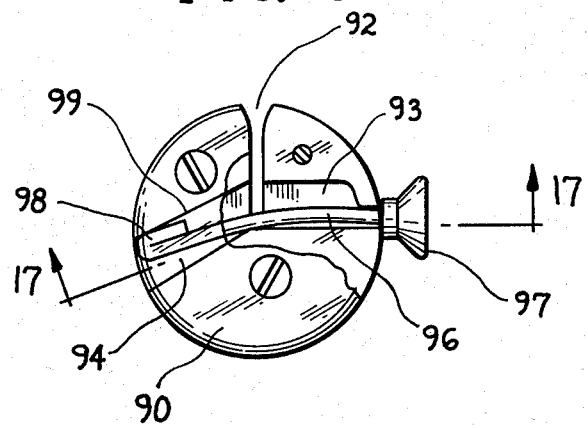
FIGS. 15 to 17 illustrate a securing device according to a fifth embodiment of the invention.
Figure 16:
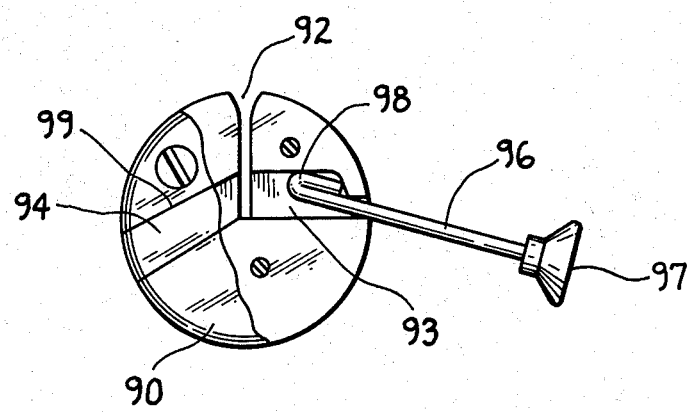
Figure 17:
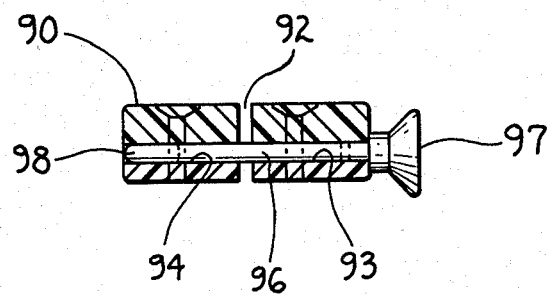

Referring now to FIGS. 15–17, a fifth embodiment of the invention is disclosed. In this embodiment a button-like body portion 90 is provided having a slot 92 extending radially therethrough to approximately the center of the body 90. Communicating with the slot 92 are a pair of channels 93, 94. Channels 93, 94 are offset from the slot 92, that is, they do not meet the slot 92 at a perpendicular intersection. Instead, they are intentionally provided in the body 90 so that each is at a slight angle from the perpendicular but in an opposite sense so that channels 93, 94 could be considered the sides of a triangle having its apex at the slot 92.

Contained within channel member 93 is a metallic spring retaining clip 96 having a gripping tab 97 on one end and a doubled-over portion 98 on the other end. Portion 98 prevents the clip 96 from being withdrawn entirely from channel 93 due to a narrowing of such channel on the periphery of the body. The advantage of this embodiment is that when the retaining clip 96 is inserted into channel 93, across slot 92 and into channel 94, the channels act as a pair of opposed incline planes for firmly pressing the retaining clip 96 against a suture which has been passed into the slot 92. As indicated best in FIG. 17, as the retaining clip 96 is inserted, it strikes wall 99 of channel 94 and the further the clip is pressed into the channel, the further it is bent, thereby increasing tension against the suture.

This arrangement can accommodate a wide variety of suture diameters because of the use of the inclined plane arrangement wherein the further the clip is inserted into the channel 94, the greater the force created against the suture. This increased pressure is maintained due to the inclined planes which cause a bending of the retaining clip 96 across a fulcrum which is at the end of slot 92, exactly where the suture is compressed against the body 90. Thus, a three-point compression of the retaining clip 96 is effected. In this manner, a device is provided which securely locks the suture in place when desired but permits rapid release of the suture for readjustment or removal merely by withdrawing the retaining clip from channel 94 in the manner described for the previous embodiments.

While we have shown and described embodiments of this invention in some detail, it will be understood that this description and illustrations are offered merely by way of example, and that the invention is to be limited in scope only by the appended claims.

We claim:
1. A device for releasably securing a suture in position over a wound, comprising:
   a cylindrical button-like member having a radially extending slot for receiving said suture therein and a channel extending therethrough intersecting said slot, said channel being formed in two complementarily inclined sections which intersect at said slot and diverge radially outwardly therefrom for exerting increasing lateral force on said compression means as it is moved to the compression position to securely lock said means in said compression position; and
   means provided in said channel and movable between a compression position and a release position for compressing said suture against said button-like member in said compression position and for releasing said suture to permit adjustment or removal in said release position.

2. The device according to claim 1 wherein said compression means is a compression clip.

3. The device according to claim 2 wherein said compression clip is a metal spring clip.

4. The device of claim 1 wherein said compression means is a metal clip, said lateral force serving to bend said clip against said button-like member at the termination of said slot to firmly secure the suture therebetween.

5. The device according to claim 4 wherein one of said inclined sections is constricted near the periphery of said button-like member and said clip is doubled over at its end to prevent said clip from being fully withdrawn from said one section.

6. The device of claim 9 wherein said doubled over clip end presses against the channel walls in said release position to hold said clip to permit manual application of the device with one hand.

* * * * *